US012616604B2

(12) United States Patent
Robinson et al.

(10) Patent No.: US 12,616,604 B2
(45) Date of Patent: May 5, 2026

(54) EXTERNAL CATHETER APPARATUS

(71) Applicants: John Robinson, Brookshire, TX (US);
Jubilee Robinson, Brookshire, TX (US)

(72) Inventors: John Robinson, Brookshire, TX (US);
Jubilee Robinson, Brookshire, TX (US)

( * ) Notice: Subject to any disclaimer, the term of this
patent is extended or adjusted under 35
U.S.C. 154(b) by 377 days.

(21) Appl. No.: 18/509,787

(22) Filed: Nov. 15, 2023

(65) Prior Publication Data

US 2025/0152405 A1     May 15, 2025

(51) Int. Cl.
*A61F 5/451* (2006.01)
*A61F 5/44* (2006.01)

(52) U.S. Cl.
CPC ............ *A61F 5/451* (2013.01); *A61F 5/4408*
(2013.01)

(58) Field of Classification Search
CPC ........ A61F 5/451; A61F 5/4408; A61F 5/453;
A61B 10/0038; A61B 10/007
See application file for complete search history.

(56) References Cited

U.S. PATENT DOCUMENTS

| | | | | |
|---|---|---|---|---|
| 4,200,102 | A | * | 4/1980 | Duhamel ................ A61F 5/451 |
| | | | | 604/353 |
| 5,342,583 | A | * | 8/1994 | Son ........................ A61F 5/451 |
| | | | | 4/453 |
| 8,882,731 | B2 | | 11/2014 | Suzuki |
| D928,946 | S | | 8/2021 | Sanchez |
| 11,207,206 | B2 | | 12/2021 | Sharma |
| 11,389,318 | B2 | | 7/2022 | Radl |
| 11,395,871 | B2 | | 7/2022 | Radl |
| 11,633,298 | B2 | | 4/2023 | Nazemi |
| 2016/0136338 | A1 | | 5/2016 | Lee |
| 2022/0370236 | A1* | | 11/2022 | Rothberg .............. A61F 5/4405 |
| 2023/0052238 | A1 | | 2/2023 | Oluwasogo |

FOREIGN PATENT DOCUMENTS

WO        WO2014208814        12/2014

* cited by examiner

*Primary Examiner* — Andrew J Mensh
*Assistant Examiner* — Hans Kaliher

(57)        ABSTRACT

An external catheter apparatus for collecting urine and feces
from a user includes a collection tube which defines an
interior space in the collection tube. The collection tube
further defines an aperture for facilitating the passage of
urine into the collection tube and a plurality of holes for
facilitating the passage of fluid feces into the collection tube.
Transfer tubes are in fluid communication with the collec-
tion tube such that the urine and feces may be drawn away
from the collection tube via suction on the transfer tubes.

7 Claims, 6 Drawing Sheets

EXTERNAL CATHETER APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to catheters and more particularly pertains to a new catheter for collecting urine and feces from a user.

(2) Description of Related Art Including Information Disclosed Under 37 CFR 1.97 and 1.98

The prior art relates to catheters, including those which lie externally below a user in order to collect urine from the user and draw the urine away from the user. However, the prior art fails to describe an external catheter with holes arranged to facilitate entry of fluid feces into the external catheter which is drawn away from the user via suction. Such an apparatus would be advantageous over the prior art by facilitating the removal of both urine and feces away from the user.

BRIEF SUMMARY OF THE INVENTION

An embodiment of the disclosure meets the needs presented above by generally comprising a collection tube which defines an interior space in the collection tube. The collection tube is elongated between a front end and a rear end and defines an aperture which extends through a top side of the collection tube to the interior space. The aperture is positioned adjacent to the front end of the collection tube and extends from the front end toward the rear end. The rear end defines a plurality of holes which extend through the rear end of the collection tube to the interior space. A length of the collection tube is such that the aperture is configured to be positioned under an opening to a urethra of a user while the plurality of holes is positioned under an anus of the user.

A urine transfer tube is coupled to the front end of the collection tube and is in fluid communication with the interior space of the collection tube. The urine transfer tube is configured to be in fluid communication with a urine suction source.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
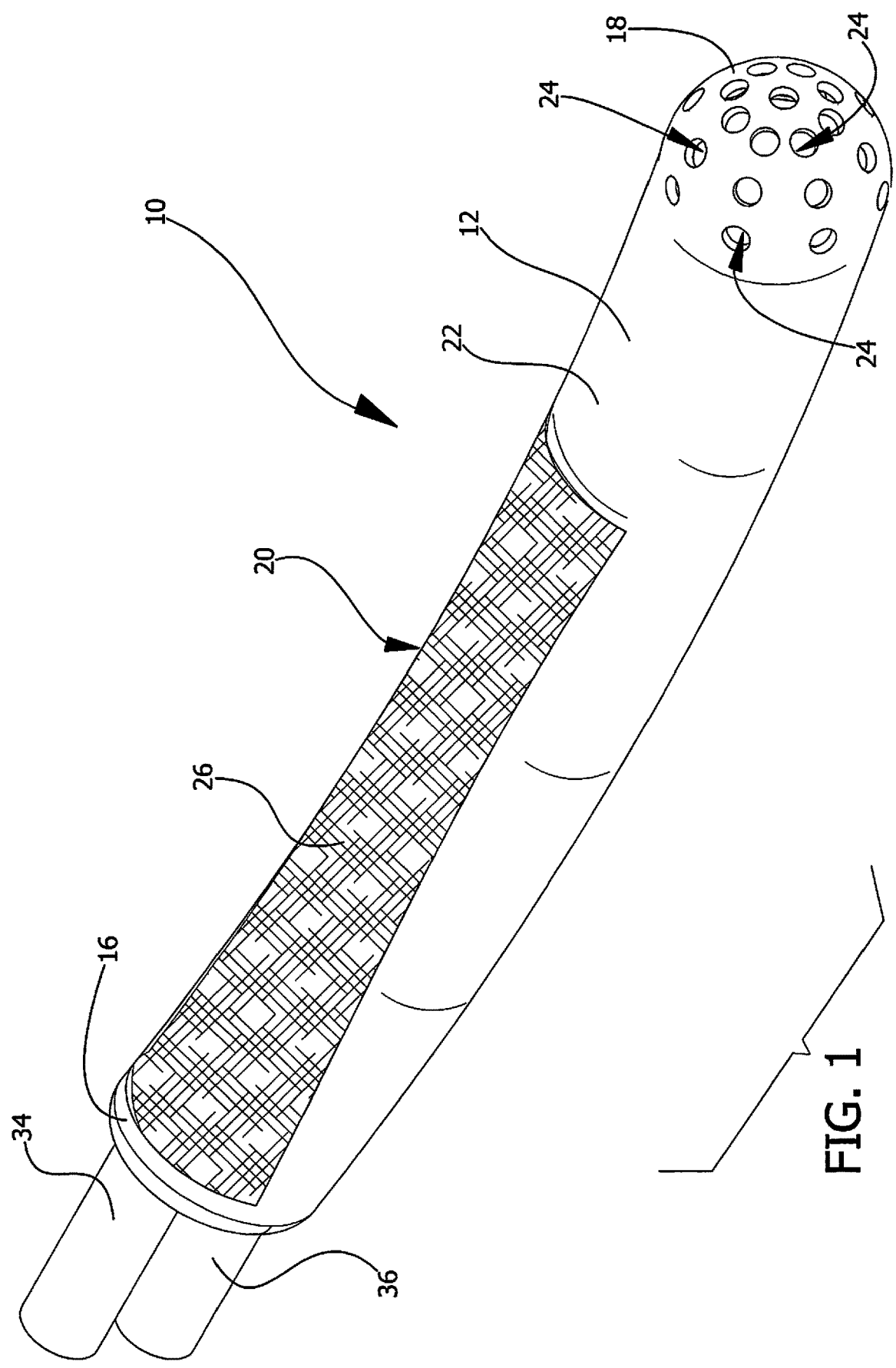
FIG. 1 is a top rear side perspective view of an external catheter apparatus according to an embodiment of the disclosure.
Figure 2:
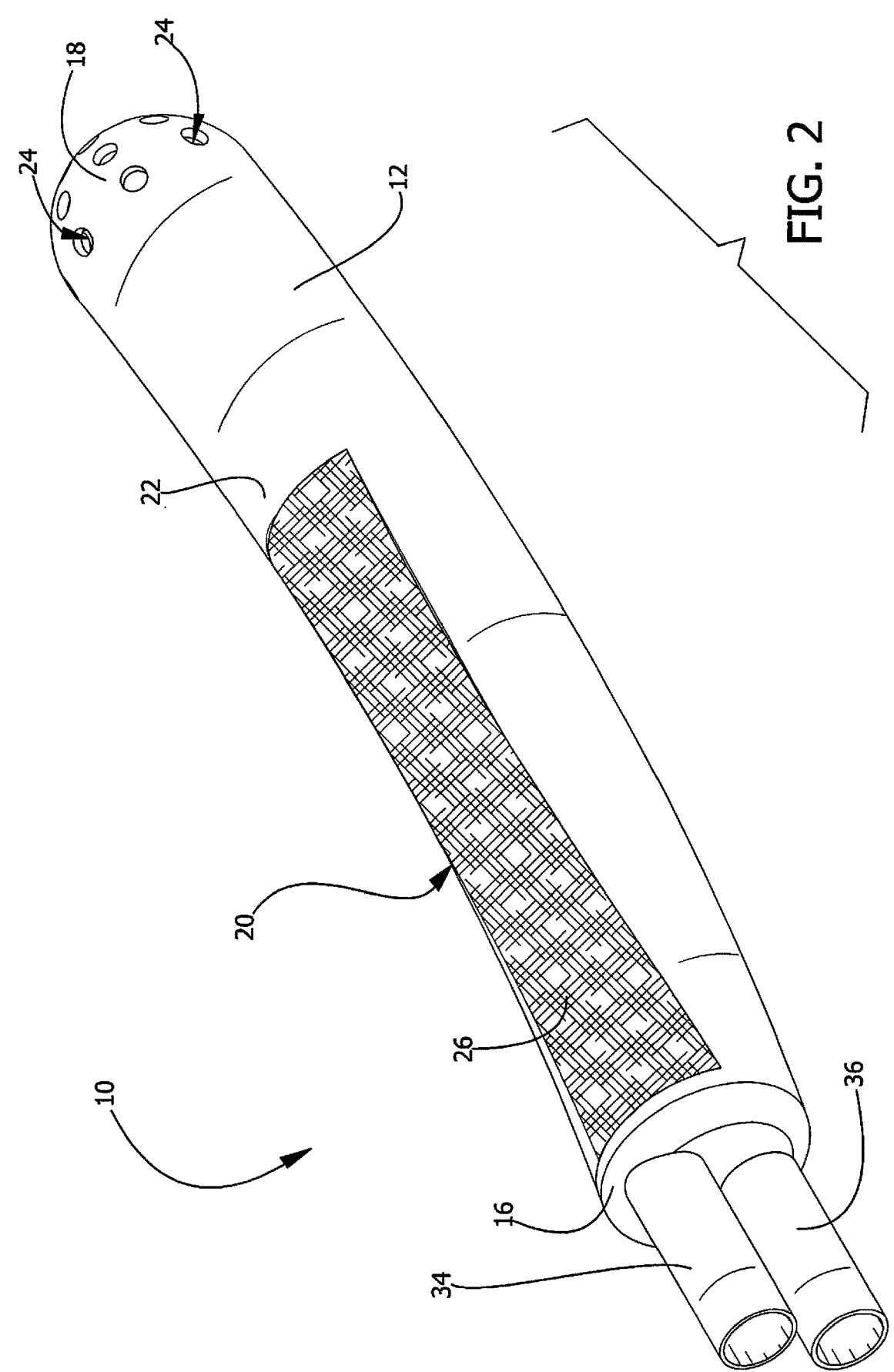
FIG. 2 is a top front side perspective view of an embodiment of the disclosure.
Figure 3:
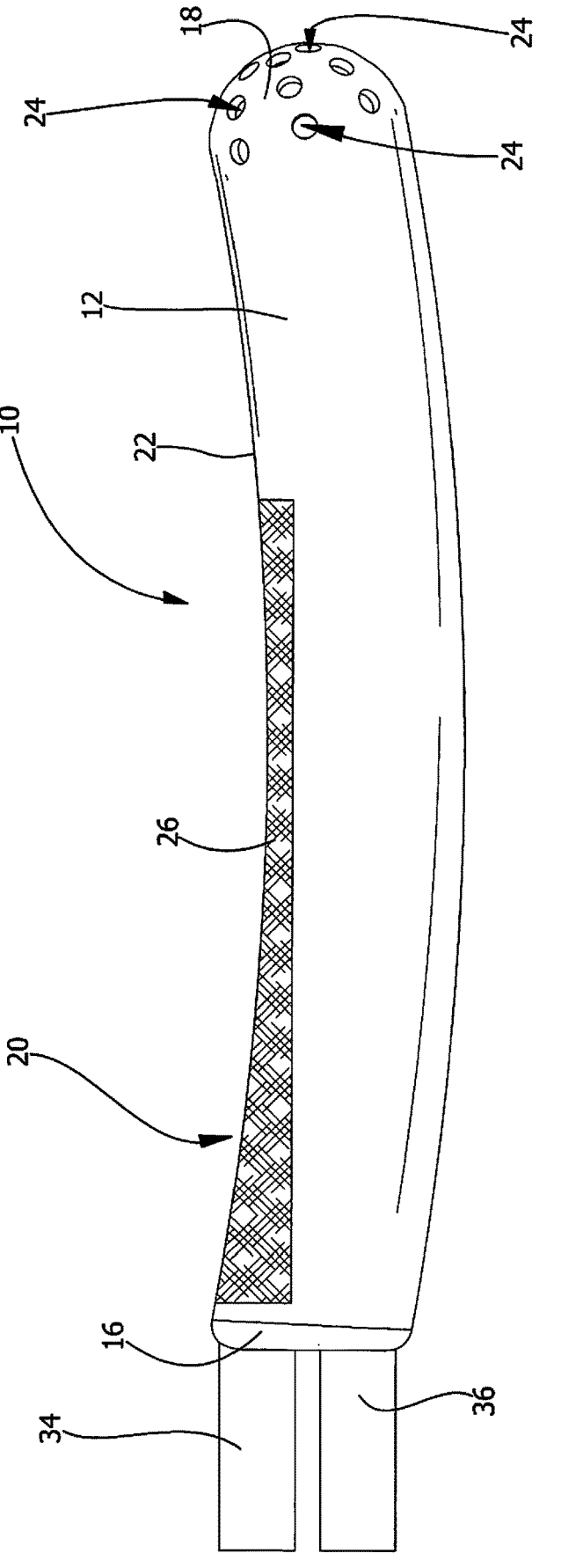
FIG. 3 is a side view of an embodiment of the disclosure.
Figure 4:
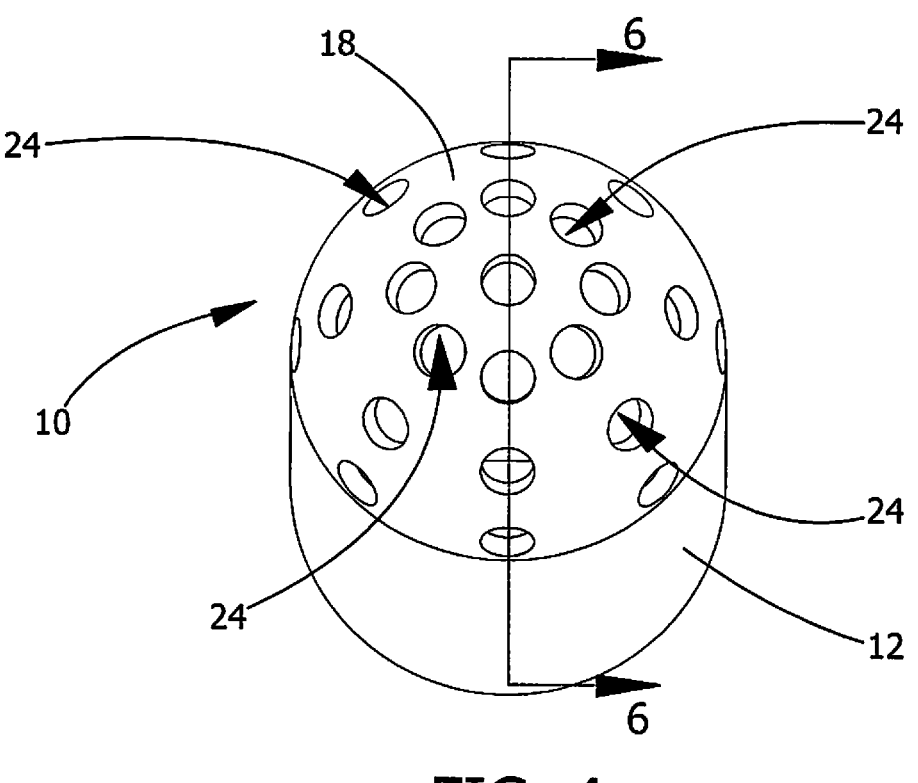
FIG. 4 is a rear view of an embodiment of the disclosure.
Figure 5:
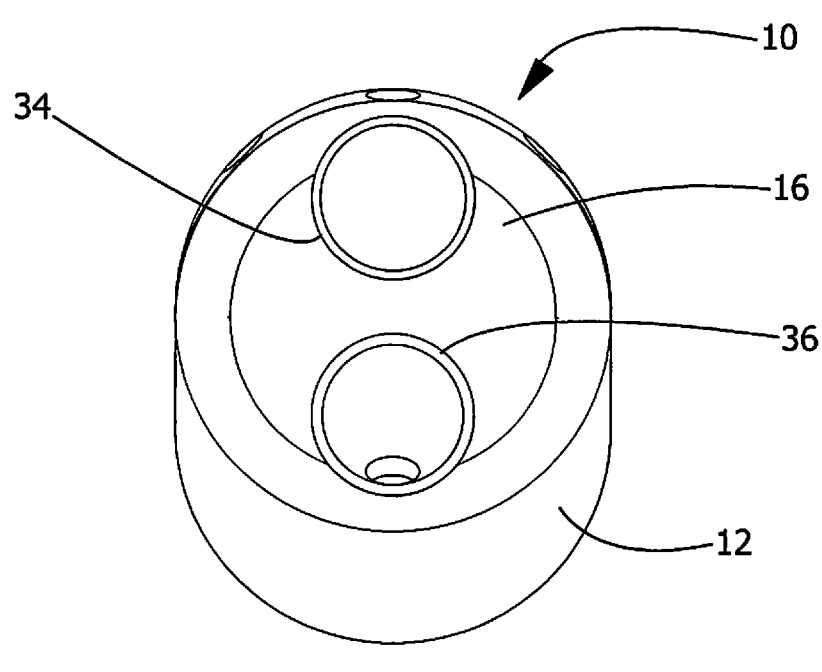
FIG. 5 is a front view of an embodiment of the disclosure.
Figure 6:
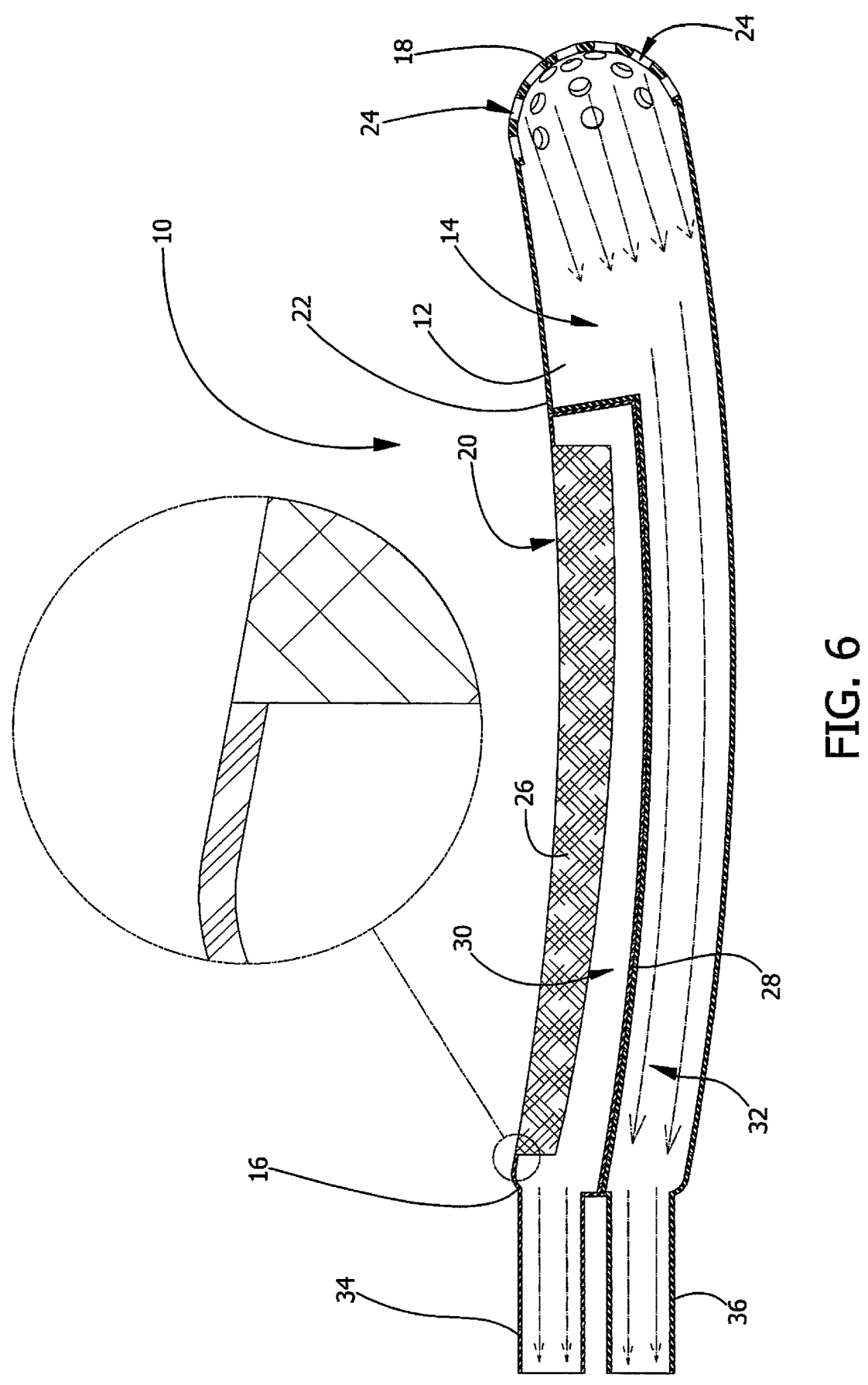
FIG. 6 is a cross section view of an embodiment of the disclosure taken from Arrows 6-6 in FIG. 4.
Figure 7:
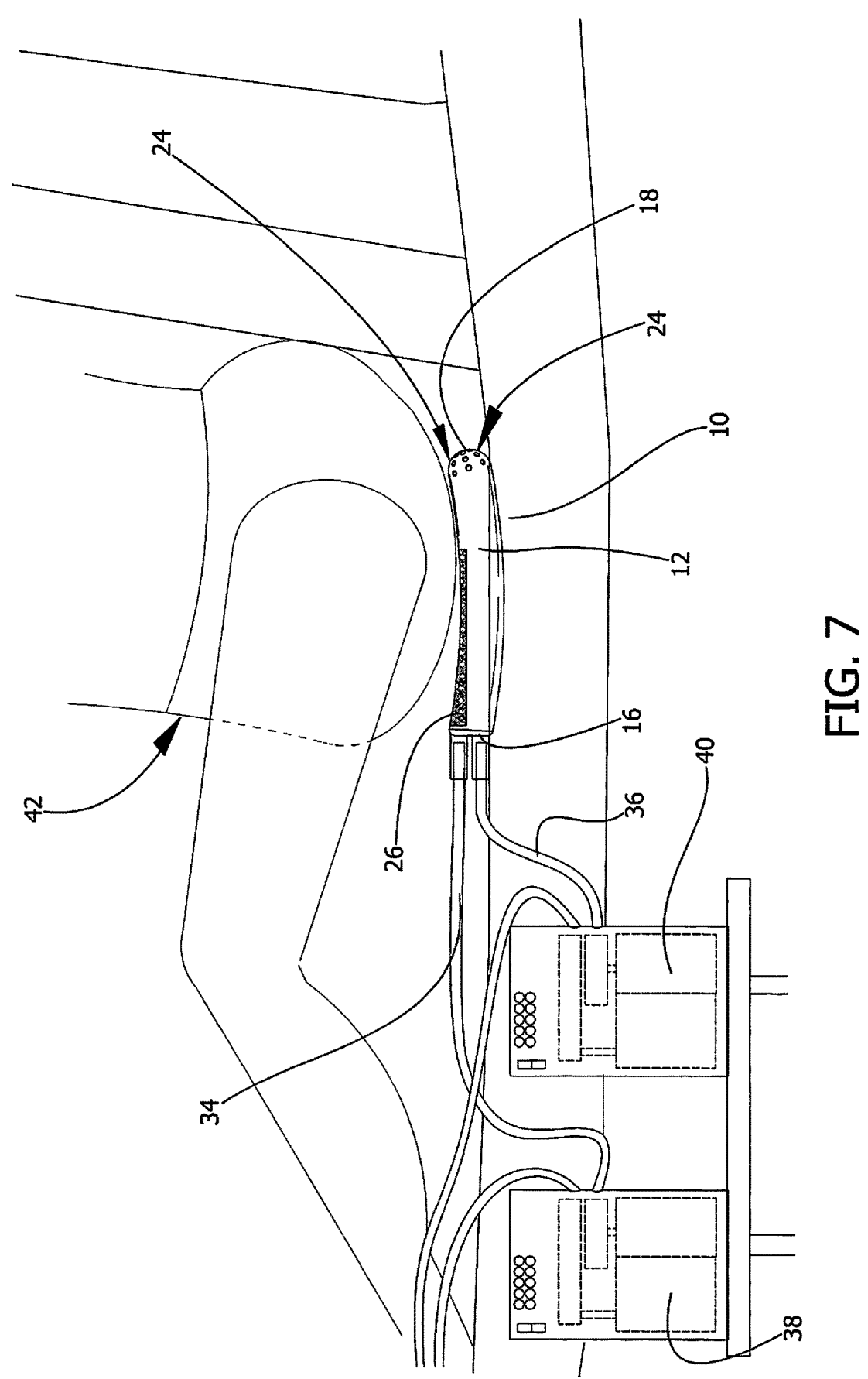
FIG. 7 is an in-use view of an embodiment of the disclosure.

With reference now to the drawings, and in particular to FIGS. 1 through 7 thereof, a new catheter embodying the principles and concepts of an embodiment of the disclosure and generally designated by the reference numeral 10 will be described.

As best illustrated in FIGS. 1 through 7, the external catheter apparatus 10 generally comprises a collection tube 12 which defines an interior space 14 in the collection tube 12. The collection tube 12 is elongated between a front end 16 and a rear end 18. The collection tube 12 defines an aperture 20 which extends through a top side 22 of the collection tube 12 to the interior space 14 and is positioned adjacent to the front end 16 of the collection tube 12. The aperture 20 extends from the front end 16 toward the rear end 18, terminating at between 50% and 75% of a length of the collection tube 12 between the front end 16 and the rear end 18. The rear end 18 has a dome shape and defines a plurality of holes 24 which extend through the rear end 18 of the collection tube 12 to the interior space 14.

The length of the collection tube 12 is such that the aperture 20 is configured to be positioned under an opening to a urethra of a user 42 while the plurality of holes 24 is positioned under an anus of the user 42. The collection tube 12 comprises a resiliently compressible material such that the collection tube 12 conforms to a body of the user 42 when the collection tube 12 is positioned against the body.

The resiliently compressible material comprises a silicone foam but may comprise a rubber foam, another polymer foam, a fabric, or the like. A urine collection gauze 26 is coupled to the collection tube 12 and covers the aperture 20. The urine collection gauze 26 is permeable to urine and comprises a moisture wicking material.

A divider wall 28 is mounted in the collection tube 12 and divides the interior space 14 into a urine chamber 30 and a feces chamber 32. The urine chamber 30 is in fluid communication with the aperture 20 of the collection tube 12, and the feces chamber 32 is in fluid communication with the plurality of holes 24 of the collection tube 12. A urine transfer tube 34 is coupled to the front end 16 of the collection tube 12 and is in fluid communication with the urine chamber 30. A feces transfer tube 36 is coupled to the front end 16 of the collection tube 12 and is in fluid communication with the feces chamber 32. The urine transfer tube 34 is configured to be in fluid communication with a urine suction source 38, and the feces transfer tube 36 is configured to be in fluid communication with a feces suction source 40.

In use, the external catheter apparatus 10 is placed under the user 42 such that the aperture 20 is positioned under the opening of the urethra of the user 42 and the plurality of holes 24 is positioned under the anus of the user 42. When the user 42 urinates, urine is collected by the urine collection gauze 26 and transferred into the urine chamber 30. Suction is applied to the urine transfer tube 34 to move the urine from the urine chamber 30 toward the urine suction source 38. When the user 42 defecates, particularly when producing fluid feces due to diarrhea or similar conditions, suction is applied to the feces transfer tube 36 to draw the produced feces into the feces chamber 32 via the plurality of holes 24 and through the feces chamber 32 and the feces transfer tube 36 toward the feces suction source 40. Some embodiments may not include a divider wall 28 and may include only one transfer tube connected to one suction source, in which case the one suction source may apply suction to urge urine and feces toward the one suction source.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An external catheter apparatus for collection of urine and fluid feces, the apparatus comprising:
a collection tube defining an interior space in the collection tube, the collection tube being elongated between a front end and a rear end, the collection tube defining an aperture which extends through a top side of the collection tube to the interior space, the aperture being positioned adjacent to the front end of the collection tube, the aperture extending from the front end toward the rear end, the rear end defining a plurality of holes which extend through the rear end of the collection tube to the interior space, a length of the collection tube being such that the aperture is configured to be positioned under an opening to a urethra of a user while the plurality of holes is positioned under an anus of the user;

a urine transfer tube being coupled to the front end of the collection tube and being in fluid communication with the interior space of the collection tube, the urine transfer tube being configured to be in fluid communication with a urine suction source;

a divider wall being mounted in the collection tube, the divider wall dividing the interior space into a urine chamber and a feces chamber, the urine chamber being in fluid communication with the aperture of the collection tube, the feces chamber being in fluid communication with the plurality of holes of the collection tube;

wherein the urine transfer tube is in fluid communication with the urine chamber; and a feces transfer tube being coupled to the front end of the collection tube and being in fluid communication with the feces chamber, the feces transfer tube being configured to be in fluid communication with a feces suction source.

2. The apparatus of claim 1, wherein the aperture extends from the front end of the collection tube toward the rear end and terminates at between 50% and 75% of the length of the collection tube between the front end and the rear end.

3. The apparatus of claim 1, wherein the rear end has a dome shape.

4. The apparatus of claim 1, wherein the collection tube comprises a resiliently compressible material such that the collection tube conforms to a body of the user when the collection tube is positioned against the body.

5. The apparatus of claim 4, wherein the resiliently compressible material comprises a silicone foam.

6. The apparatus of claim 1, further comprising a urine collection gauze being coupled to the collection tube and covering the aperture, the urine collection gauze being permeable to urine, the urine collection gauze comprising a moisture wicking material.

7. An external catheter apparatus for collection of urine and fluid feces, the apparatus comprising:
a collection tube defining an interior space in the collection tube, the collection tube being elongated between a front end and a rear end, the collection tube defining an aperture which extends through a top side of the collection tube to the interior space, the aperture being positioned adjacent to the front end of the collection tube, the aperture extending from the front end toward the rear end, the aperture terminating at between 50% and 75% of a length of the collection tube between the front end and the rear end, the rear end defining a plurality of holes which extend through the rear end of the collection tube to the interior space, the rear end having a dome shape, the length of the collection tube being such that the aperture is configured to be positioned under an opening to a urethra of a user while the plurality of holes is positioned under an anus of the user, the collection tube comprising a resiliently compressible material such that the collection tube conforms to a body of the user when the collection tube is positioned against the body, the resiliently compressible material comprising a silicone foam;

a divider wall being mounted in the collection tube, the divider wall dividing the interior space into a urine chamber and a feces chamber, the urine chamber being in fluid communication with the aperture of the collection tube, the feces chamber being in fluid communication with the plurality of holes of the collection tube;

a urine collection gauze being coupled to the collection tube and covering the aperture, the urine collection gauze being permeable to urine, the urine collection gauze comprising a moisture wicking material;

a urine transfer tube being coupled to the front end of the collection tube and being in fluid communication with the urine chamber, the urine transfer tube being configured to be in fluid communication with a urine suction source; and a feces transfer tube being coupled to the front end of the collection tube and being in fluid communication with the feces chamber, the feces transfer tube being configured to be in fluid communication with a feces suction source.

* * * * *